United States Patent [19]

Bornkamm et al.

[11] Patent Number: 5,798,230
[45] Date of Patent: Aug. 25, 1998

[54] PROCESS FOR THE PREPARATION OF HUMAN MONOCLONAL ANTIBODIES AND THEIR USE

[75] Inventors: Georg Wilhelm Bornkamm, München; Dirk Eick, Germering, both of Germany; Bettina Kempkes, Chestnut Hill, Mass.; Nicola Maria Jochner, Freising; Lothar J. Strobl, Germering, both of Germany

[73] Assignee: GSF-Forschungszentrum fur Umwelt und Gesundheit GmbH, Oberschleissheim, Germany

[21] Appl. No.: 626,860

[22] Filed: Apr. 3, 1996

[30] Foreign Application Priority Data

Nov. 9, 1995 [DE] Germany ............... 195 41 844.1

[51] Int. Cl.$^6$ ............... C12P 21/04; C12P 21/06
[52] U.S. Cl. ............... 435/70.21; 435/69.1; 435/325; 435/172.3; 435/320.1; 530/350
[58] Field of Search ............... 435/172.3, 69.1, 435/70.21, 320.1; 530/350

[56] References Cited

PUBLICATIONS

Goossens, D. et al. 1987. J. Immunol. Methods, 101:193–200.

Cohen, J. I et al. 1989. Proc. Natl. Acad. Sci. USA, 86:9558–9562.

Benjamin, D. et al. 1982. J. Immunol.129:1336–1342.

Picard, D. et al. 1988. Cell; 54:1073–1080.

Kempkes, B. et al., "B–cell proliferation and induction of early $G_1$–regulating proteins by Epstein–Barr virus mutants conditional for EBNA2", *The EMBO Journal*, vol. 14, No. 1, 88–96 (1995).

*Primary Examiner*—Lila Feisee
*Assistant Examiner*—Minyh-Tam Davis
*Attorney, Agent, or Firm*—Skjerven, Morrill, MacPherson,Franklin & Friel; Emily M. Haliday LLP

[57] ABSTRACT

The present invention provides a process for the preparation of human monoclonal antibodies from human B cells. According to this process, human antibody-producing B cells are immortalized by infection with an Epstein-Barr virus, or derivative thereof, that expresses Epstein-Barr virus nuclear antigen 2 (EBNA2). EBNA2 function, which is required for immortalization, is subsequently shut off, which results in an increase in antibody production. The invention provides a variety of systems that allow expression of EBNA2 function to achieve immortalization, followed by reduction of EBNA2 expression or function to facilitate antibody production.

11 Claims, 6 Drawing Sheets

PROCESS FOR THE PREPARATION OF HUMAN MONOCLONAL ANTIBODIES AND THEIR USE

BACKGROUND OF THE INVENTION

1. Field of the Invention

The present invention relates to a process for the preparation of human monoclonal antibodies and to their use.

2. Description of the Related Art

Antibodies are widely used in the treatment and therapy of humans. Antibodies are used in immunoprophylaxis, in the treatment of acute infections, and in the treatment of immunosuppressed patients. At the present time human antibodies are not to be prepared in a sufficient amount. A process of the generic type is set forth e. g. in Casali et al., (1986). Science 234, 476–479.

For this reason animal antibodies are frequently employed. One disadvantage of animal antibodies is that they cause interfering immune responses and loose their activity. Human antibodies can be obtained from human serum. This process, however, shows three fundamental disadvantages: suitable human serum is available only in a restricted amount, all of the purified antibodies are polyclonal, the treatment is very expensive.

Epstein-Barr virus (EBV) is a lymphotropic herpes virus causing infectious mononucleosis. The infectious mononucleosis, also called Pfeiffer's disease, is a lymphoproliferative disease leading to hyperplasia and hypertrophy of lymphatic tissue combined with characteristic blood count alterations. EBV infects primary resting B cells giving rise to lymphoblastoid cell lines (LCLs), which are characterized by unlimited proliferation in vitro, a process synonymously called immortalization or transformation. EBV is also associated with several human disease states including Burkitt's lymphoma (BL), nasopharyngeal carcinoma, lymphomas in immunocompromised individuals, and Hodgkin's disease (cf. reviews in Miller, 1990; Klein, 1994; Masucci and Ernberg, 1994).

In LCLs only a subset of viral genes is expressed, the expressed viral genes coding for six nuclear proteins, three membrane proteins, and two small nonpolyadenylated nuclear RNAs. The minimal set of genes required for transformation is unknown to date. The EBNA2 gene is deleted in the transformation-defective virus produced by the Burkitt lymphoma cell line P3HR1. In natural isolates it appears in two allelic forms (EBNA2A and EBNA2B) which share about 50% homology (Zimber et al., 1986). EBNA2, together with EBNA-LP, is the first viral gene expressed after infection of primary B cells and is a transcriptional activator of latent viral as well as latent cellular genes (CD21, CD23, and c-fgr) (Calender et al., 1987; Wang et al., 1987; Cordier et al., 1990; Ghosh and Kieff, 1990; Fahraeus et al., 1990; Abbot et al., 1990;

Knutson, 1990; Woisetschlaeger et al., 1991; Zimber-Strobl et al., 1991; Sung et al., 1991; Jin and Speck, 1992; Ling et al., 1993; Laux et al., 1994a; Meitinger et al., 1995).

EBNA2 has been shown to exert its transactivating function at least in part by binding to an ubiquitously expressed cellular gene, RBP-Jk, which binds to the DNA in a sequence specific manner (Zimber-Strobl et al., 1994; Henkel et al., 1994; Grossmann et al., 1994; Waltzer et al., 1994), and through interaction with transcription factors of the ets gene family (SPi-1, PU-1) (Laux et al., 1994b; and Johannsen et al., 1995). Even though the transformation of primary B cells in vitro is strictly dependent on EBNA2 (Cohen et al., 1989; Hammerschmidt and Sugden, 1989; Kempkes et al., 1995) EBNA2 appears not to be expressed in BL tumors (Rowe et al., 1986), Hodgkin's disease (Kanavaros et al., 1993), and nasopharyngeal carcinomas (Fahraeus et al., 1988; Young et al., 1988) thus questioning its role in the development of these disease states in vivo.

SUMMARY OF THE INVENTION

The aim of the present invention is to develop a process of the aforementioned type in a way that monoclonal human antibodies can be prepared in a sufficient amount and with high specificity.

This aim is achieved by means of the characteristic features of claims 1 and 12. The dependent claims describe advantageous embodiments of the present process. The antibodies prepared by the process of the present invention are employed preferably as therapeutic agents in a pharmaceutical preparation.

The present process makes it possible for the first time to produce human antibodies in cell culture in such amounts that allow for purification of the antibodies and for their medical utilization.

In the following the present invention is illustrated in more detail by preferred embodiments; however, the present invention is not meant to be limited to those. Further embodiments can be achieved by one skilled in the art without being inventive.

Thus, according to the present invention antibody-producing B cells are first infected with an Epstein-Barr virus or a naturally occurring as well as a genetically engineered derivative thereof. In a further embodiment of the present invention a vector is used which has at least those sequences of the Epstein-Barr virus necessary for immortalization of human B cells. Preferably primary human B cells are infected.

DETAILED DESCRIPTION OF THE INVENTION

For a better understanding of the role of EBNA2 in the process of B cell transformation a conditional system has been developed wherein the function of the EBNA2 protein can be reversibly switched on and off. Using the conditional system developed by Picard et al. (1988) and Eilers et al. (1989) the hormone binding domain of the estrogen receptor has been fused to the N- or C-terminal of EBNA2 thus rendering the function of the EBNA2 protein dependent on the presence or absence of estrogen. As expected the chimeric EBNA2 proteins exhibit their transactivating function on viral and cellular genes only in the presence of estrogen.

According to the present invention it has been surprisingly found that the surface IgM expression and the transcription of the Ig μ locus is very efficiently decreased by the EBNA2 protein. EBNA2 thus functions as a negative regulator of the Ig μ transcription.

Figure 1:
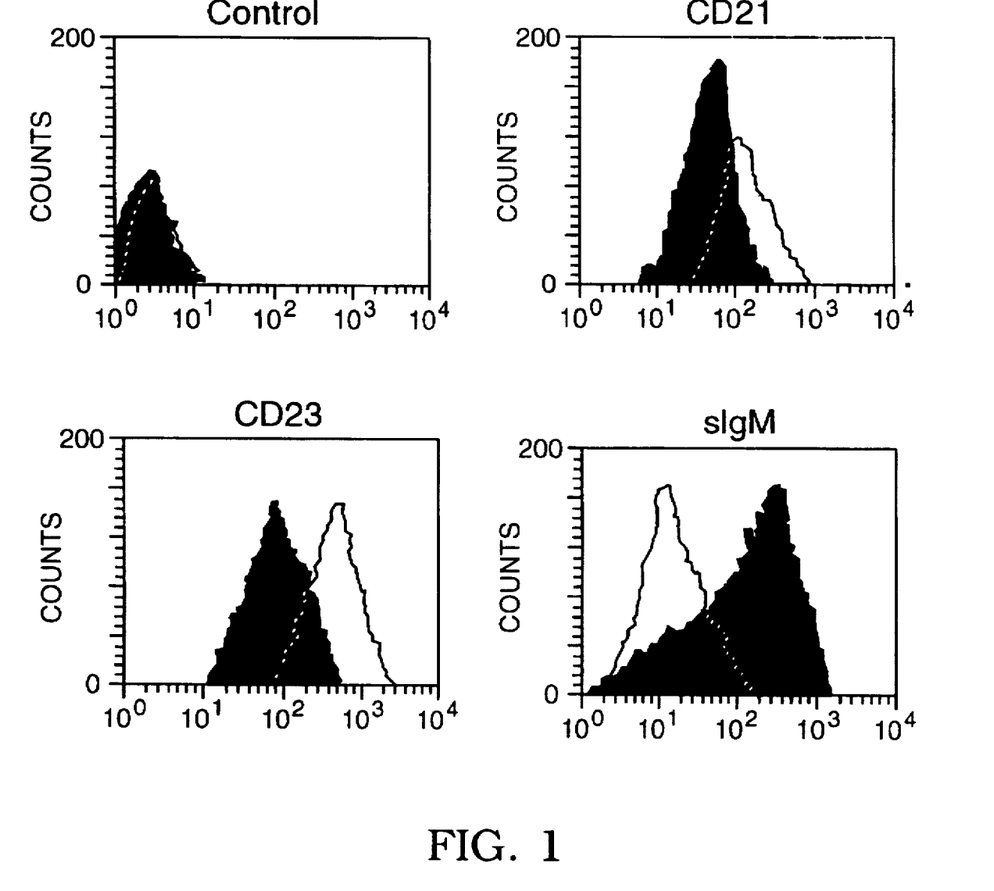
FIG. 1 shows a flow cytometeric analysis of estrogen-treated (white histograms) and estrogen-deprived (black histograms) lymphoblastoid cell lines expressing an EBNA2-estrogen binding domain fusion protein after staining for CD21, CD23, and surface IgM.
Figure 2:
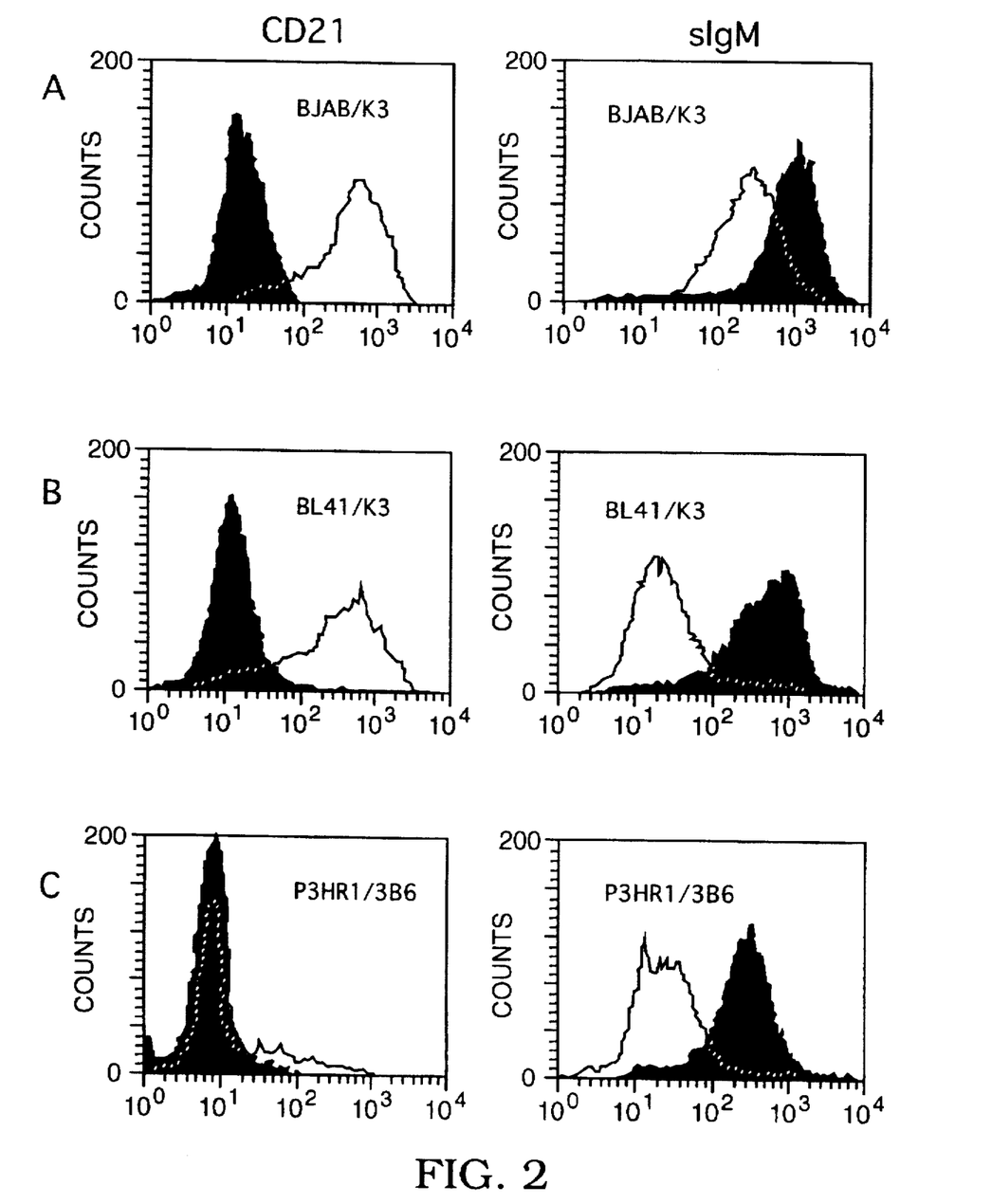
FIG. 2 shows the expression of CD21 and surface IgM in the presence (white histograms) and absence (black histograms) of EBNA2 activity in two Burkitt's lymphoma cell lines.
Figure 3:
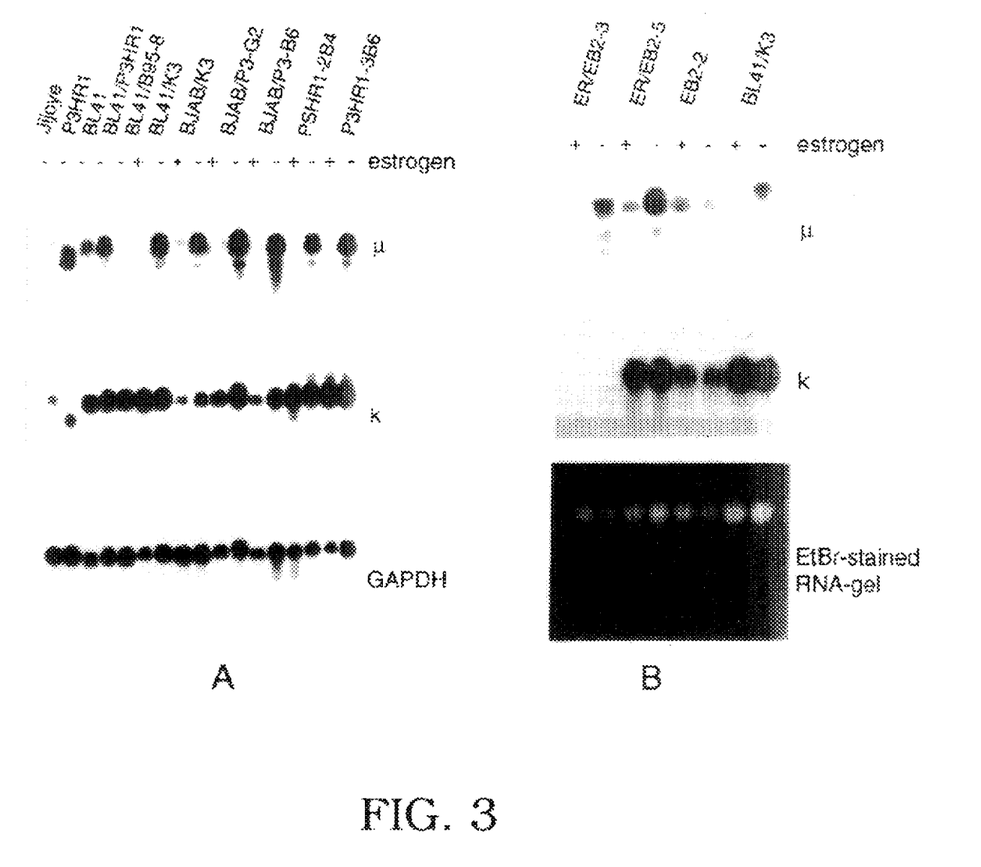
FIG. 3 shows the suppression of expression of the Ig μ heavy chain by EBNA2 in B lymphoma cells and in lymphoblastoid cells.
Figure 4:
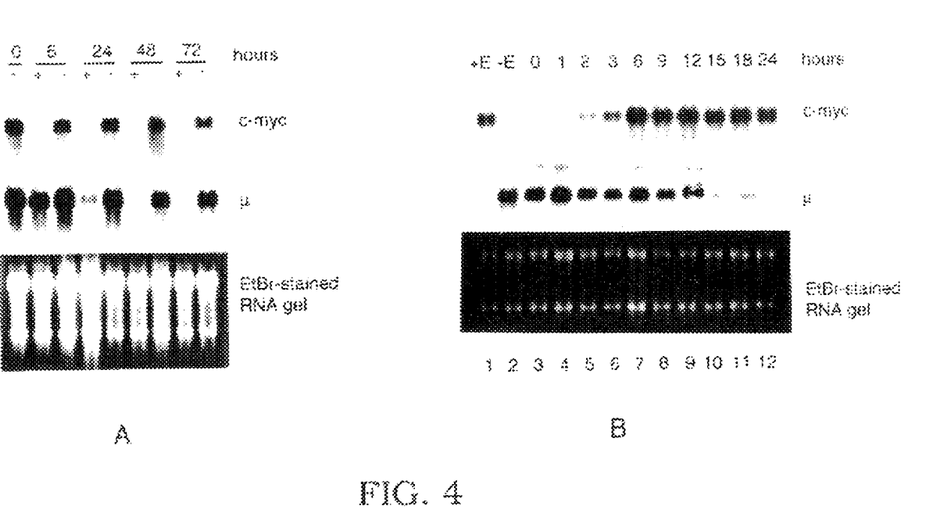
FIG. 4 demonstrates the co-regulation of Ig μ and c-myc expression in Burkitt's lymphoma cells expressing an EBNA2-estrogen binding domain fusion protein.

In the following the present invention is illustrated in more detail by the following exemplary embodiments using the Figures, wherein FIGS. 1 and 2 show by way of example the increase in immunoglobulin protein production resulting from switching off of EBNA2. The FIGS. 3 and 4 show the corresponding production of immunoglobulin RNA.

The present invention is based on the surprising finding that B cells infected by Epstein-Barr virus produce only minor amounts of immunoglobulin whereas the production is increased 100-fold following inactivation of EBNA2 function.

The present invention is described in more detail in the exemplary embodiments with respect to an IgM-producing B cell line. The present invention, however, shall not be limited to such an IgM-producing B cell line but according to the invention B cells expressing different immunoglobulin classes, e. g. IgG and IgA, can be immortalized.

The source of the B cells used is generally a human having a high titer of antibodies for the desired antigen. Cells are preferably obtained from the peripheral blood, and B cells are enriched according to standard methods, and infected with a virus derived from Epstein-Barr virus expressing a conditional EBNA2. During infection and proliferation of the B cells the EBNA2 function has to be in an activated state. The virus described by Kempkes et al. (1995), EMBO J. 14, 88–96, is particularly preferred for infection (cf. FIG. 5 and the subsequent description). For activation of the EBNA2 function it is necessary to add estrogen to the culture medium to ensure constitutive EBNA2 function. The immortalized B cells are expanded and diluted several times with medium containing estrogen until the desired number of cells is obtained. The cells are plated in a low cell density in 96-well flat bottom plates and again expanded. The cellular supernatant is tested for the desired specific antibodies. B cells producing the highly specific antibodies are used as the basis for the preparation of antibodies.

In these B cell clones the EBNA2 activity is switched off by washing out the estrogen. Other methods for estrogen removal can be also applied. Alternatively, the activity of the EBNA2 gene may also be controlled by using the hormone binding domain of the androgen receptor or another hormone binding domain, or on a transcriptional level by using inducible promoters for the EBNA2 gene. By switching off the EBNA2 function the immunoglobulin production within the B cells is increased steadily and after 2 days has been increased up to about 100-fold. 4 days, death of a large proportion of the cells occurs.

Another embodiment of the invention employs cell lines producing monoclonal antibodies immortalized with EBV or EBV-derived vectors, which are known in the art. Prior to the present invention, such cell lines produced antibodies only in amounts of less than 1 μg/ml. However, one embodiment of the present invention is a method for obtaining a dramatic increase in antibody production from such cells.

In this embodiment, human antibody-producing B cells are infected or transfected with an Epstein-Barr virus or a derivative thereof in a first culture medium. Said virus or derivative expresses at least a functional Epstein-Barr virus nuclear antigen 2 (EBNA2) protein. Expressing of at least said EBNA2 protein will produce immortalized B cells.

Said immortalized B cells are screened for specificity for a desired antigen to identify an immortalized B cell clone producing monoclonal antibodies specific for the desired antigen. Said identified B cell clone is propagated in said first culture medium to obtain a desired amount of B cells.

A vector is introduced into the B cells which is capable of expressing a genetically altered dominantly negative form of an EBNA2 protein. The genetically altered form of said EBNA2 protein can inhibit activity of the wild type EBNA2 protein. There are several possibilities for introducing said genetically altered dominantly negative form of said EBNA2 protein. Either transfection or infection can be used. A vector capable of expressing said genetically altered dominantly negative EBNA2 protein can be transfected or infected into the human antibody-producing B cells, before or after infection with an Epstein-Barr virus or a derivative thereof, or into said propagated B cell clone producing monoclonal antibodies.

The wild type form of EBNA2 consists of 487 amino acids. A suitable genetically altered dominantly negative form of the EBNA2 protein is truncated at the carboxy terminus, and, in one embodiment, the deletion comprises amino acids 150–487. This truncated EBNA2 protein forms functionally inactive heterodimers with the functional EBNA2 protein thereby inhibiting the functional EBNA2 protein.

In a first variation of this embodiment, the nucleotide sequence encoding said genetically altered EBNA2 protein is operatively linked with a nucleotide sequence that provides inducible expression of said nucleotide sequence encoding said genetically altered EBNA2.

In a second variation of this embodiment, the nucleotide sequence encoding the genetically altered EBNA2 is fused, in functional connection, with a nucleotide sequence including a hormone-binding domain to produce a fusion gene encoding a fusion protein comprising said genetically altered EBNA2 fused to said hormone-binding domain. The genetically altered EBNA2 can be fused at its N- or C-terminus to said hormone-binding domain. This fusion protein inhibits functional EBNA2, as described above, when a hormone specific for the hormone-binding domain binds to the fusion protein, i.e., hormone binding activates the inhibitory function of the genetically altered dominantly negative EBNA2 protein. In preferred embodiments of the invention, said hormone-binding domain binds estrogen or an androgen.

When the hormone-binding domain is an estrogen-binding domain, for example, the identified B cell clone is propagated in the absence of estrogen, and a few days before harvesting monoclonal antibodies, the cells are treated with estrogen. By this estrogen treatment, said genetically altered EBNA2 protein is activated and thereby the endogenous functional EBNA2 protein present in the cells is inhibited. This process effects the production of monoclonal antibodies in considerably larger quantities than any process known in the art.

In the following the construction of a plasmid is described that is useful for the expression of conditional EBNA2 function. The plasmid includes the EBNA2 gene or a derivative thereof. The present invention shall, however, not be limited to the plasmid illustrated herein. According to the invention other vectors can be used by which EBNA2 function can be conditionally expressed, i.e., its function is at least partly switched on upon immortalization of the B cells and is at least partly switched off prior to recovery of the antibodies. Preferably EBNA2 function is substantially switched on for immortalization and is substantially switched off for antibody recovery.

EXAMPLE

Figure 6:
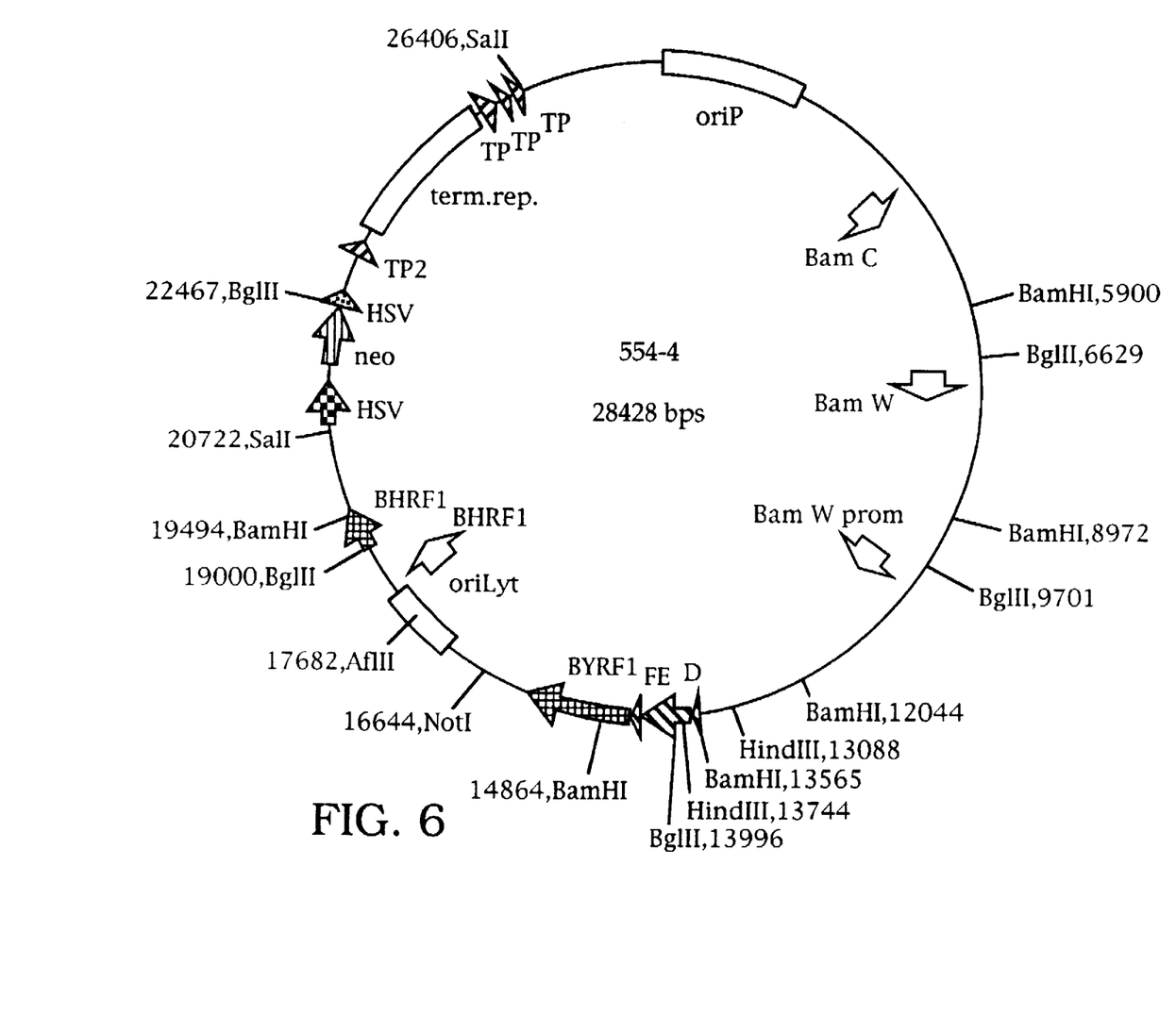
FIG. 6 shows a restriction map of an ER/EBNA2 mini-EBV plasmid according to the present invention.

The hormone binding domain of the estrogen receptor was fused to either the N- or the C-terminal end of the open reading frame (ORF) of EBNA2 resulting in plasmids ER/EBNA2 and EBNA2/ER. Both plasmids had the overall structure of the mini-EBV p554 expressing wild-type EBNA2, EBNA-LP, and the open reading frame BHRF1 (Hammerschmidt and Sugden, 1989). The N-terminal fusion construct was generated by introducing an EcoRI restriction site immediately 5' to the ORF of EBNA2 by in vitro mutagenesis. The gene fragment encoding the hormone binding domain was generated by the polymerase chain reaction (PCR) using HE14 (Kumar et al., 1986) as a template flanked by EcoRI recognition sites and ligated into the EcoRI site preceding the EBNA2 ORF. This PCR fragment included the Kozak's sequence provided by HE14 but excluded the stop codon of the estrogen receptor. A restriction map of a preferred ER/EBNA2 mini-EBV plasmid is shown in FIG. 6. The hormone binding domain starts at position 13565 (D in FIG. 6) and includes the complete receptor domain (DEF). The C-terminal fusion construct was generated by inserting BglII and EcoRI recognition sites immediately before the stop codon of EBNA2 by in vitro mutagenesis. A BamHI-EcoRI fragment of HE14 coding for the hormone binding site of the estrogen receptor was ligated into the BglII-EcoRI sites at the end of EBNA2. The subsequent cloning steps regenerated EBV strain B95.8 with the coordinates 13944–54364 (cf. Baer et al., 1984) with two alterations: the NotI repeats were deleted, and only two BamHI W repeats were inserted.

Figure 5:
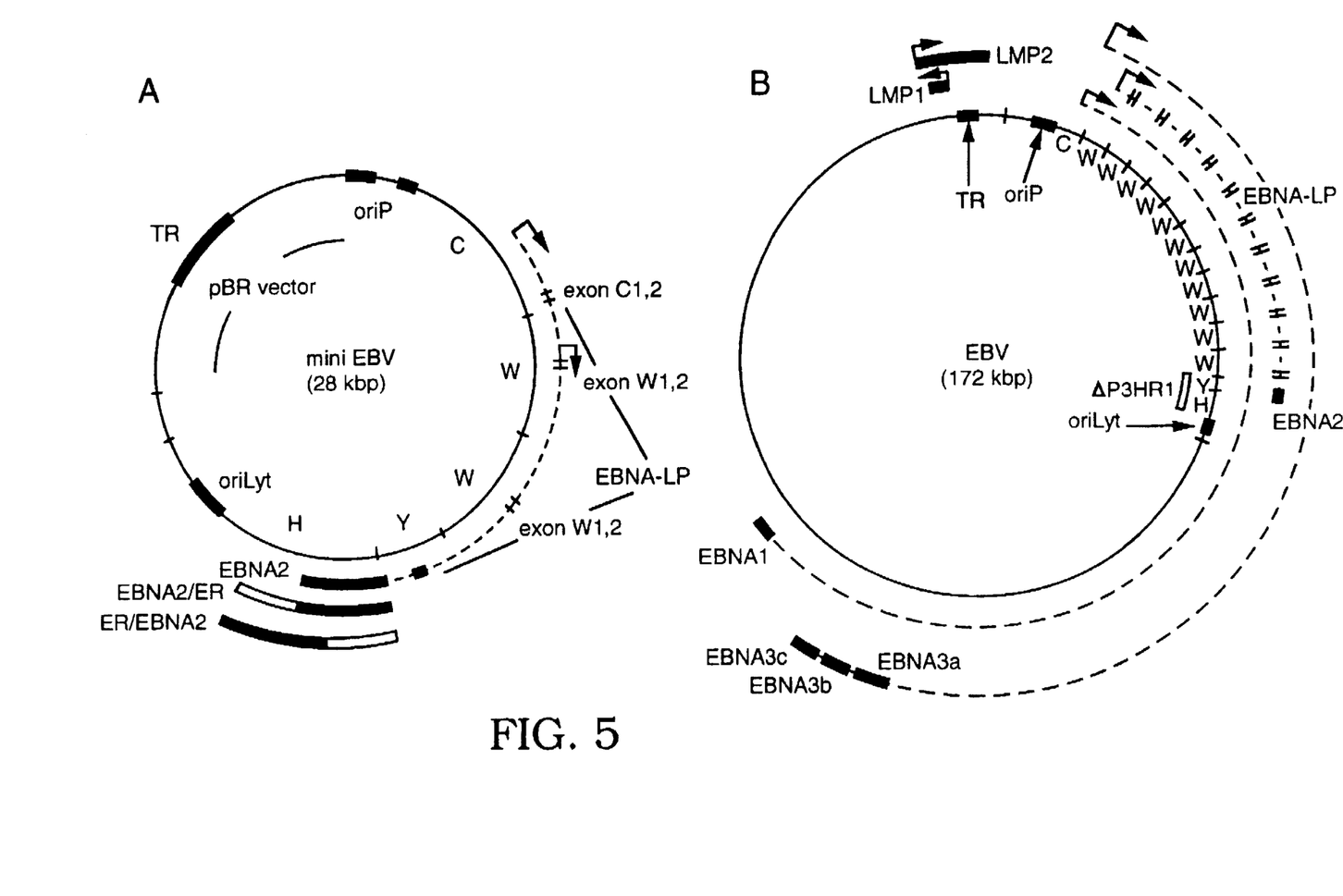
FIG. 5A shows a mini-EBV plasmid according to the present invention.
FIG. 5B shows a map of EBV strain B95.8.

FIG. 5 illustrates the strategy for the expression of conditional EBNA2 mutants in growth-transformed B cells.

(A) FIG. 5 shows mini-EBV plasmids composed of cis-acting elements essential for the propagation of these plasmids in all phases of the Epstein-Barr virus life cycle. These mini-EBV plasmids carry the plasmid origin of replication (orip) required for the maintenance of the EBV plasmids in the target cells, the lytic origin of replication (oriLyt) which allows amplification to high copy number upon induction of the lytic replication of the virus, and the terminal repeats (TR) permitting packaging of the mini-EBV plasmids into virions. Mini-EBV plasmids are employed with a helper virus, such as P3HR1, that provides for amplification and packaging of the plasmids.

The hormone binding domain of the estrogen receptor (white boxes) was fused to either the C- or the N-terminus of the wild-type EBNA2 open reading frame (black boxes) leading to the EBNA2/ER and the ER/EBNA2 mutant respectively. The EBNA2 expression cassettes are flanked by BamHI restriction fragments C, W, Y, and H of the EBV genome representing in part the genomic organization of the DNA of EBV, and including the deletion (ΔP3HR1, open bar in B) also present in the non-transforming EBV strain P3HR1. EBNA2 as well as EBNA2 mutants can be transcribed from two alternative promotors localized in the C or W fragments.

The FIG. 5 (B) represents the map of EBV strain B95.8, showing the EBNAs and LMPs (latent membrane proteins) transcribed in growth-transformed B cells, and the localization of the promotors thereof with respect to the BamHI restriction map of this strain.

The estrogen dependent cell lines ER/EB2-3 and ER/EB2-5 are lymphoblastoid cell lines (LCLs) established by coinfection of primary B cells by P3HR1 virus and a mini-EBV plasmid expressing ER/EBNA2 and complementing the EBNA2 defect of P3HR1 virus in trans (Kempkes et al., 1995). Briefly, P3HR1 cells, which carry the P3HR1 virus, were transfected with mini-EBV plasmids and simultaneously induced for lytic cycle replication. Supernatants of the transfected cells containing mini-EBVs together with the P3HR1 helper virus were harvested and used to coinfect primary B cells.

The estrogen independent EB2-2 cell line was generated simultaneously using wild type EBNA2 to complement the EBNA2 defect of the P3HR1 virus. BL41 is an EBV-negative BL cell line bearing a t(8;14) translocation (Lenoir et al., 1985). BL41/P3HR1 and BL41/B95-8 are BL41 cells stably infected (converted) by P3HR1 or B95-8 virus respectively (Calender et al., 1987). BJAB is an EBV-negative B lymphoma cell line (Klein et al., 1974); BJAB/P3 is a BJAB cell line stably infected by P3HR1 virus. P3HR1 is a single cell clone of the EBV-positive B cell line Jijoye containing a t(8;14) translocation (Hinuma et al., 1967). Jijoye produces an EBNA2 competent virus, P3HR1 cells an EBNA2 defective virus (Bornkamm et al., 1982). The lymphoma cell lines expressing ER/EBNA2 are described by Kempkes et al. All cell lines were cultured in RPMI1640 medium supplemented with 10% fetal calf serum, 100 U/ml penicillin and streptomycin, and 1 mM pyruvate. β-estradiol (Merck, Darmstadt) was added to the cell culture medium at a final concentration of 1 μM.

For FACS analysis 1×10⁶ cells were incubated with an excess of unlabeled monoclonal mouse antibodies directed against CD21 (BL13) and surface IgM (AF6) (Dianova, Hamburg). FITC (fluorescein) conjugated goat anti mouse F(ab)₂ fragments (DAKO, Hamburg) were used as secondary antibody to stain positive cells. Dead cells were identified, and after propidium iodide staining (0.1 μg/ml) excluded from analysis. The samples were analyzed using a FACSSCAN device (Becton and Dickinson). 3-H thymidine incorporation assay was performed as described in Kempkes et al., 1995.

Northern blot analysis was performed as described in Eick and Bornkamm, 1989. The 1.2 kb EcoRI/EcoRI fragment and the constant region 0.9 kb EcoRI/SacI fragment described in Eick et al. (1985) were used as Ig μ gene probes.

The lymphoblastoidal cells transformed with the conditional EBNA construct described above were tested for expression of surface markers prior to and after removal of estrogen.

The FIG. 1 shows a flow cytometric analysis of estrogen treated (white histograms) and estrogen deprived (black histograms) ER/EB2-5 cells after staining for CD21, CD23, and surface IgM.

The FIG. 1 particularly shows the amount of IgM antibodies produced by an EBV immortalized B cell in the presence (white area) and in the absence (black area) of EBNA2 activity after elapse of two days. Comparable results were obtained for two other cell lines following immortalization of primary B cells with the above mentioned virus.

The FIG. 1 demonstrates that the expression of CD23 and to a lesser extent of CD21 was decreased by switching off the function of EBNA2 by removal of estrogen. At the same time, however, the expression of IgM was strongly increased. Increase of IgM expression and decrease of CD21 and CD23 expression were reversible since the expression of CD21 as well as CD23 increased, and the expression of IgM decreased upon following readdition of estrogen. Those results are not detailed herein.

Decrease of surface IgM may either be mediated by EBNA2 itself or by other viral targets located downstream (e. g. the viral latent membrane proteins) induced by EBNA2. To discriminate between these possibilities, the mini-EBV plasmid expressing the ER/EBNA2 fusion protein was stably introduced into the EBV-negative B cell lymphoma lines BL 41 and BJAB, and for comparison also into P3HR1 cells. In the stably transfected cell lines the activation of the TP1 or the LMP1 promotor was strictly dependent on the presence of estrogen indicating that the ER/EBNA2 protein is indeed functional in these cells. FACS analysis prior and after addition of estrogen revealed a strong decrease of expression of sIgM (surface IgM) after addition of estrogen (FIG. 2).

This leads to the conclusion that the decrease in expression of sIgM is a function of EBNA2 and not a function of any other viral target gene.

Northern blot analysis was carried out to detect the level at which IgM expression is downregulated by EBNA2. By including RNA of paired cell lines differing in the presence or absence of the wild-type EBNA2 gene the Northern blot analysis further provided an answer to the question whether the decrease in IgM is caused not only by the EBNA2-estrogen receptor fusion protein but also by wild-type EBNA2. The paired cell lines included P3HR1 producing an EBNA2 defective virus, and its parental cell line Jijoye having a functional EBNA2 gene (EBNA2B allele) and BL41 cells stably infected/converted by P3HR1 virus (BL41/P3HR1) or the transformation competent EBNA2 wild-type positive virus B95-8 having the EBNA2A allele. As becomes apparent from FIG. 3, EBNA2 downregulates the surface expression of IgM by decrease of the Ig μ RNA.

The FIG. 2 shows the amount of IgM antibodies produced in the presence (white area) and absence (black area) of EBNA2 activity in two Burkitt lymphoma cell lines after 2 days.

The FIG. 2 particularly demonstrates the suppression of cell surface IgM by EBNA2 in B lymphoma cell lines. Cells transfected with the mini-EBV plasmid expressing ER/EBNA2 (BJAB/K3, BL41/K3, and P3HR1/3B6) were cultured for two days in the presence (white histograms) or in the absence (black histograms) of 1 μM β-estradiol and then were analyzed for cell surface CD21 and expression of surface IgM by FACS analysis. 1×10⁶ cells were incubated with excess of unlabeled mouse monoclonal antibodies recognizing human CD21 (BL13) or IgM (AF6). FITC conjugated goat anti mouse F(ab)₂ fragments were used as secondary antibody to stain positive cells. Control cells were marked exclusively with secondary antibodies but showed no alterations following addition of estrogen (data not shown). Dead cells were identified, and after propidum iodide staining (0.1 μg/ml) excluded from analysis.

The FIGS. 3 and 4 represent correspondingly the amount of the equivalent immunoglobin RNAs.

The FIG. 3 particularly shows the suppression of the expression of the Ig μ heavy chain by EBNA2 in B lymphoma cells and in LCLs. Total cellular RNA was isolated from Jijoye, P3HR1, BL41, BL41/ P3HR1, BL41/ B95-8, and ER/EBNA2 transfected cells cultured for two days in the presence or in the absence of estrogen (A), or from LCL cell lines expressing the ER/EBNA2 protein (ER/EB2-3 and ER/EB2-5) or the wild-type EBNA2 protein (EB2-2), the cell lines having been treated with estrogen or deprived of estrogen for four days (B), isolated, and the cells were analyzed with respect to Ig μ heavy chain, Ig k light chain and GAPDH RNA by Northern blot analysis.

The FIG. 4 demonstrates the co-regulation of Ig μ and c-myc gene expression in ER/EBNA2 transfected BL cells. P3HR1/3B6 cells (A) were treated with estrogen (+) for the period indicated and tested for expression of Ig μ and c-myc RNA by Northern blot analysis. The ethidium bromide stained gels are shown at the bottom of the Figure. In estrogen dependent LCLs the Ig μ and c-myc expression are regulated oppositely to each other by estrogen (B).

By using the process of the present invention it is possible for the first time to provide human B cell derived antibodies in large amounts. For this purpose B cells are used which have been immortalized by EBV or a derivative of EBV and containing the EBNA2 gene in a conditional form. For immortalization of the B cells the EBNA2 gene is switched on, and for production of antibodies the EBNA2 gene is switched off.

The supernatants of cell cultures are harvested preferably between days 2 and 5, and the antibodies are purified. The latter are then available for therapeutic purposes. Processes for recovery of the antibodies are familiar from the state of the art, and can be readily applied to the present process by one skilled in the art.

The antibodies are preferably employed in those cases where animal antibodies or manipulated animal antibodies may lead to undesirable side effects in humans.

All publications referred to herein are hereby expressly incorporated by reference in their entirety as indicative of the level of skill in the art.

Literature

Abbot, S. D., Rowe, M., Cadwallader, K., Ricksten, A., Gordon, J., Wang, F., Rymo, L. and Rickinson, A. B. (1990). Epstein-Barr virus nuclear antigen 2 induces expression of the virus encoded latent membrane protein. *J. Virol.* 64, 2126–2134.

Albert, T., Urlbauer, B., Kohlhuber, F., Hammersen, B. and Eick, D. (1994). Ongoing mutations in the N-terminal domain of c-Myc affect transactivation in Burkitt's lymphoma cell lines. *Oncogene* 9, 759–763.

Allen, R. W., Trach, K. A. and Hoch, J. A. (1987). Identification of the 37-kDa protein displaying a variable interaction with the erythroid cell membrane as glyceraldehyde-3-phophate dehydrogenase. *J. Biol. Chem.* 262, 649–653.

Benjamin, D., Magrath, L. T., Maguire, R., Janus, C., Todd, H. D. and Parsons, R. G. (1982). Immunoglobulin secretion by cell lines derived from african and american undifferentiated lymphomas of Burkitt's and non-Burkitt's type. *J. Immunol.* 129, 1336–1342.

Bornkamm, G. W., Hudewentz, J., Freese, U. K. and Zimber, U. (1982). Deletion of the nontransforming Epstein-Barr virus strain P3HR-1 causes fusion of the large internal repeat to the DSL region. *J. Virol.* 43, 952–968.

Bornkamm, W., Polack, A. and Eick, D. (1988). In Klein, G. (ed.), Cellular oncogene activation; c-myc Deregulation by Chromosomal Translocation in Burkitt's Lymphoma. M. Dekker, Inc., New York, Basel, pp 223–273.

Calender, A., Billaud, M., Aubry, J. P., Banchereau, J., Vuillaume, M. and Lenoir, G. M. (1987).

Epstein-Barr virus (EBV) induces expression of B-cell activation markers on in vitro infection of EBV-negative B-lymphoma cells. *Proc. Natl. Acad. Sci. U.S.A.* 84, 8060–8064.

Cohen, J. I., Wang, F., Mannick, J. and Kieff, E. (1989). Epstein-Barr virus nuclear protein 2 is a key determinant of lymphocyte transformation. *Proc. Natl. Acad. Sci. U.S.A.* 86, 9558–9562.

Cohen, J. H. M., Revillard, J. P., Magaud, J. P., Lenoir, G., Vuillaume, M., Manel, A. M., Vincent, C. and Bryon, P. A. (1987). B-cell maturation stages of Burkitt's lymphoma cell lines according to Epstein-Barr virus status and type of chromosome translocation. *J. Natl. Cancer Inst.* 78, 235–242.

Cordier Bussat, M., Billaud, M., Calender, A. and Lenoir, G. M. (1993). Epstein-Barr virus (EBV) nuclear-antigen-2-induced up-regulation of CD21 and CD23 molecules is dependent on a permissive cellular context. *Int. J. Cancer* 53, 153–160.

Cordier, M., Calender, A., Billaud, M., Zimber, U., Rousselet, G., Pavlish, O., Banchereau, J., Tursz, T., Bornkamm, G. and Lenoir, G. M. (1990). Stable transfection of Epstein-Barr virus (EBV) nuclear antigen 2 in lymphoma cells containing the EBV P3HR1 genome induces expression of B-cell activation molecules CD21 and CD23. *J. Virol.* 64, 1002–1013.

Crawford, D. H. and Ando, I. (1986). EB virus is associated with B-cell maturation. *Immunology* 59, 405–409.

Dani, C., Blanchard, J. M., Piechaczyk, M., El Sabouty, S., Marty, L. and Jeanteur, J. (1984). Extreme instability of myc mRNA in normal and transformed human cells. *Proc. Natl. Acad. Sci. U.S.A.* 81, 7046–7050.

Eick, D., Piechaczyk, M., Henglein, B., Blanchard, J.-M., Traub, B., Kofler, E., Wiest, S., Lenoir G. M. and Bornkamm, G. W. (1985). Aberrant c-myc RNAs of Burkitt's lymphoma cells have longer half lives. *EMBO J.* 4, 3717–3725.

Eick, D. and Bornkamm, G. W. (1989). Expression of normal and translocated c-myc alleles in Burkitt's lymphoma cells: evidence for different regulation. *EMBO J.* 8, 1965–1972.

Eilers, M., Picard, D., Yamamoto, K. R. and Bishop, J. M. (1989). Chimaeras of myc oncoprotein and steroid receptors cause hormone-dependent transformation of cells. *Nature* 340, 66–68.

Fahraeus, R., Fu, H. L., Ernberg, I., Finke, J., Rowe, M., Klein, G., Falk, K., Nilsson, E., Yadav, M., Busson, P., Tursz, T. and Kallin, B. (1988). Expression of Epstein-Barr virus-encoded proteins in nasopharyngeal carcinoma. *Int. J. Cancer* 42, 329–338.

Fahraeus, R., Jansson, A., Ricksten, A., Sjoblom, A. and Rymo, L. (1990). Epstein-Barr virus encoded nuclear antigen 2 activates the viral latent membrane protein promoter by modulating the activity of a negative regulatory element. *Proc. Natl. Acad. Sci. U.S.A.* 87, 7390–7394.

Ghosh D. and Kieff, E. (1990). Cis-acting regulatory elements near the Epstein-Barr virus latent-infection membrane protein transcriptional start site. *J. Virol.* 64, 1855–1858.

Grossman, S. R., Johannsen, E., Tong, X., Yalamanchili, R. and Kieff, E. (1994). The Epstein-Barr virus nuclear antigen 2 transactivator is directed to response elements by the Jκ recombination signal binding protein. *Proc. Natl. Acad. Sci. USA* 91, 7568–7572.

Hammerschmidt, W. and Sugden, B. (1989). Genetic analysis of immortalizing functions of Epstein-Barr virus in human B lymphocytes. *Nature* 340, 393–397.

Henkel, T., Ling, P. D., Hayward, S. D. and Peterson, M. G. (1994). Mediation of Epstein-Barr Virus EBNA2 Transactivation of by Recombination Signal-Binding protein Jκ. *Science* 265, 92–95.

Hieter, P. A., Max, E. E., Seidman, J. G., Maizel, J. V. Jr. and Leder, P. (1980). Cloned human and mouse kappa immunoglobulin constant and J region genes conserve homology in functional segments. *Cell* 22, 197–207.

Hinuma, Y., Konn, M., Yamaguchi, J., Wudarski, D. J., Blakeslee, J. R., Jr. and Grace, J. T., Jr. (1967). Immunofluorescence and herpes-type virus particles in the P3HR-1 Burkitt lymphoma cell line. *J. Virol.* 1, 1045–1051.

Jack, H. M. and Wabl, M. (1988). Immunoglobulin mRNA stability varies during B lymphocyte differentiation. *EMBO J.* 7, 1041–1046.

Jin, X. W. and Speck, S. H. (1992). Identification of critical cis elements involved in mediating Epstein-Barr virus nuclear antigen 2-dependent activity of an enhancer located upstream of the viral BamHI C promoter. *J. Virol.* 66, 2846–2852.

Johannsen, E., Koh, E., Mosialos, G., Tong, X., Kieff, E., Grossman, S. R. (1995). Epstein-Barr virus nuclear protein 2 transactivation of the latent membrane protein 1 promoter is mediated by Jκ and PU.1. *J. Virol.* 69, 253–262.

Kanavaros, P., Jiwa, M., van-der-Valk, P., Walboomers, J., Horstman, A. and Meijer, C. J. (1993). Expression of the Epstein-Barr virus latent gene products and related cellular activation and adhesion molecules in Hodgkin's disease and non-Hodgkin's lymphomas arising in patients without overt pre-existing immunodeficiency. *Hum. Pathol.* 24, 725–729.

Kaye, K. M., Izumi, K. M. and Kieff, E. (1993). Epstein-Barr virus latent membrane protein 1 is essential for B-lymphocyte growth transformation. *Proc. Natl. Acad. Sci. U.S.A.* 90, 9150–9154.

Kempkes, B., Spitkovsky, D., Jansen-Dürr, P., Ellwart, J., Kremmer, E., Delecluse, H. J., Rottenberger, C., Bornkamm, G. W. and Hammerschmidt, W. (1995). B-cell proliferation and induction of early G1-regulating proteins by Epstein-Barr virus mutants conditional for EBNA2. *EMBO J.*, 14, 88–95.

Kieff, E. and Liebowitz, D. (1990). Epstein-Barr Virus and Its Replication. In Virology. B. N. Fields, D. N. Knipe, R. M. Chanock, M. S. Hirsch, J. L. Melnick, T. P. Monath, and B. Roizman, eds. (New York: Raven Press), pp. 1889–1920.

Klein, G. (1994). Epstein-Barr virus strategy in normal and neoplastic B cells *Cell* 77, 791–793.

Klein, G., Lindahl, T., Jondal, M., Leibold, W., Menezes, J., Nilsson, K. and Sundstrom, C. (1974). Continuous lymphoid cell lines with characteristics of B cells (bone-marrow-derived), lacking the Epstein-Barr virus genome and derived from three human lymphomas. *Proc. Natl. Acad. Sci. U.S.A.* 71, 3283–3286.

Knutson, J. C. (1990). The level of c-fgr RNA is increased by EBNA-2, an Epstein-Barr virus gene required for B-cell immortalization. *J. Virol.* 64, 2530–2536.

Laux, G., Dugrillon, C., Eckert, B., Adam, B., Zimber-Strobl, U. and Bornkamm, G. W. (1994a). Identification and characterization of an Epstein-Barr virus nuclear antigen 2-responsive element in the bidirectional promoter region of latent membrane protein and terminal protein 2 genes. *J. Virol.* 68, 6947–6958.

Laux, G., Adam, B., Strobl, L. J. and Moreau-Gachelin, F. (1994b). The Spi-1/PU.1 and Spi-B ets family transcription factors and the recombination signal binding protein RBP-Jκ interact with an Epstein-Barr virus nuclear antigen 2 responsive cis-element. *EMBO J.* 13, 5624–5632.

Lenoir, G. M., Vuillaume, M. and Bonnardel, C. (1985). Burkitt's Lymphoma: *a Human Cancer Model*. The use of lymphomatous and lymphoblastoid cell lines in the study of Burkitt's lymphoma. IARC. Sci. Publ. 309–318.

Le Roux, A., Kerdiles, B., Walls, D., Declieu, J. F. and Perricaudet, M. (1994). The Epstein-Barr virus nuclear antigens EBNA3A, -3B, and -3C repress EBN-A2-mediated transactivation of the vital terminal protein 1 gene promoter. *Virology* 205, 596–602.

Ling, P. D., Rawlins, D. R. and Hayward, S. D. (1993). The Epstein-Barr virus immortalizing protein EBNA-2 is targeted to DNA by a cellular enhancer-binding protein. *Proc. Natl. Acad. Sci. U.S.A.* 90, 9237–9241.

Madisen, L. and Groudine, M. (1994). Identification of a locus control region in the immunoglobulin heavy-chain locus that deregulates c-myc expression in plasmacytoma and Burkitt's lymphoma cells. *Genes Dev.* 8, 2212–2226.

Magrath, I. T., Freeman, C. B., Pizzo, P., Gadek, J., Jaffe, E., Santaella, M., Hammer, C., Frank, M., Reaman, G. and Novikovs, L. (1980). Characterization of lymphoma-derived cell lines: comparison of cell lines positive and negative for Epstein-Barr virus nuclear antigen. II. Surface markers. *J. Natl. Cancer Inst.* 64, 477–483.

Marcu, K. B., Bossone, S. A. and Patel, A. J. (1992). myc function and regulation. *Annu. Rev. Biochem.* 61, 809–860.

Marshall, D. and Sample, C. (1995). Epstein-Barr virus nuclear antigen 3C is a transcriptional regulator. *J. Virol.* 69, 3624–3630.

Masucci, M. G. and Ernberg, I. (1994). Epstein Barr-virus: adaption to a life within the immune system. *Trends Microbiol.* 2, 125–130.

Matsunami, N., Hamaguchi, Y., Yamamoto, Y., Kuze, K., Kangawa, K., Matsuo, H., Kawaichi, M. and Honjo, T. (1989). A protein binding to the J kappa recombination sequence of immunoglobulin genes contains a sequence related to the integrase motif. *Nature* 342, 934–937.

Meitinger, C., Strobl, L. J., Marshall, G., Bornkamm, G. W. and Zimber-Strobl, U. (1994). Crucial sequences within the Epstein-Barr virus TP1—promoter for EBNA2 mediated transactivation and interaction of EBNA2 with its responsive element. *J. Virol.* 68, 7497–7506.

Miller, G. (1990). In: Virology. Epstein-Barr virus: biology, pathogenesis, and medical aspects. B. N. Fields, D. N. Knipe, R. M. Chanock, M. S. Hirsch, J. L. Melnick, T. P. Monath, and B. Roizman, eds. (New York: Raven Press), pp. 1921–1958.

Nishikura, K., ar-Rushdi, A., Erikson, J., deJesus, E., Dugan, D. and Croce, C. (1984). Repression of rearranged μ gene and translocated c-myc in mouse 3T3 cells x Burkitt lymphoma cell hybrids. *Science* 224, 399–402.

Picard, D., Salser, S. J. and Yamamoto, K. R. (1988). A movable and regulable inactivation function within the steroid binding domain of the glucocorticoid receptor. *Cell* 54 1073–1080.

Robertson, R. S., Grossmann, S., Johannsen, E., Miller, C., Lin, J., Tomkinson, B. and Kieff, E. (1995). Epstein-Barr virus nuclear protein 3C modulates transcription through interaction with the sequence-specific DNA binding protein Jκ. *J. Virol.* 69, 3108–3116.

Rabson, M., Gradoville, L., Heston, L. and Miller, G. (1982). Non-immortalizing P3J-HR1 Epstein-Barr virus: a deletion mutant of its transforming parent, Jijoye. *J. Virol.* 44, 834–844.

Robertson, K. D., Barletta, J, Samid, D. and Arebinder, R. F. (1994). Pharmacologic activation of expression of immunodominant vital antigens: a new strategy for the treatment of Epstein-Barr-virus-associated malignancies. *Current Topics in Microbiol. and Immunol.* 194, 145–154.

Rochford, R., Hobbs, M. V., Garnier, J. L., Cooper, N. L. and Cannon, M. J. (1993). Plasmocytoid differentiation of Epstein-Barr virus-transformed B cells in vivo is associated with reduced *Proc. Natl. Acad. Sci. U.S.A.* 90, 352–356.

Rochford, R. and Mosier, D. E. (1995). Differential Epstein-Barr virus expression in B-cell subsets recovered from lymphomas in SCID mice after transplantation of human peripheral blood lymphocytes. *J. Virol.* 69, 150–155.

Rowe, D. T., Rowe, M., Evan, G. I., Wallace, L. E., Farrell, P. J. and Rickinson, A. B. (1986). Restricted expression of EBV latent genes and T-lymphocyte-detected membrane antigen in Burkitt's lymphoma cells. *EMBO J.* 5, 2599–2607.

Spencer C. A. and Groudine, M. (1991). Control of c-myc regulation in normal and neoplastic cells. *Adv. Cancer Res.* 56, 1–48.

Sung, N. S., Kenney, S., Gutsch, D. and Pagano, J. S. (1991). EBNA-2 transactivates a lymphoid-specific enhancer in the BamHIC promoter of Epstein-Barr virus. *J. Virol.* 65, 2164–2169.

Tomkinson, B., Robertson, E. and Kieff, E. (1993). Epstein-Barr virus nuclear proteins EBNA3A EBNA-3C are essential for B-lymphocyte growth transformation. *J. Virol.* 67, 2014–2025.

Waltzer, L., Logeat, F., Brou, C., Israel, A., Sergant, A. and Manet, E. (1994). The human Jκ recombination signal sequence binding protein (RBP-Jκ) targets the Epstein-Barr virus, EBNA2 protein to its DNA responsive elements. *EMBO J.* 13, 5633–5638.

Wang, F., Gregory, C. D., Rowe, M., Rickinson, A. B., Wang, D., Birkenbach, M., Kikutani, H., Kishimoto, T. and Kieff, E. (1987). Epstein-Barr virus nuclear antigen 2 specifically induces expression of the B-cell activation antigen CD23. *Proc. Natl. Acad. Sci. U.S.A.* 84, 3452–3456.

Wendel-Hansen, V., Rosen, A. and Klein, G. (1987). EBV-transformed lymphoblastoid cell lines down-regulate EBNA in parallel with secretory differentiation. *Int. J. Cancer* 39, 404–408.

Woisetschalaeger, M., Jin, X. W., Yandava, C. N., Furmanski, L. A., Strominger, J. L. and Speck, S. H. (1991). Role of the Epstein-Barr virus nuclear antigen 2 in viral promoter switching during initial stages of infection. *Proc. Natl. Acad. Sci. U.S.A.* 88, 3942–3946.

Yates, J., Warren, N., Reisman, D. and Sugden, B. (1984). A cis-acting element from the Epstein-Barr vital genome that permits stable replication of recombinant plasmids in latently infected cells. *Proc. Natl. Acad. Sci. U.S.A.* 81, 3806–3810.

Young, L. S., Dawson, C. W., Clark, D., Rupani, H., Busson, T., Tursz, T., Johnson, A. and Rickinson, A. B. (1988). Epstein-Barr virus gene expression in nasophryngeal carcinoma. *J. Gen. Virol.* 69, 1051–1065.

Zimber, U., Adldinger, H., Lenoir, G. M., Vuillaume, M., v. Knebel-Doeberitz, M., Laux, G., Desgranges, C., Wittmann, P., Freese, U. K., Schneider, U. and Bornkamm, G. W. (1986). Geographical prevalence of two types of Epstein-Barr virus. *Virology* 154, 56–66.

Zimber-Strobl, U., Suentzenich, K. O., Laux, G., Eick, D., Cordier, M., Calender, A., Billaud, M., Lenoir, G. M. and Bornkamm, G. W. (1991). Epstein-Barr virus nuclear antigen 2 activates transcription of the terminal protein gene. *J. Virol.* 65, 415–423.

Zimber-Strobl, U., Kremmer, E., Grässer, F., Marschall, G., Laux, G. and Bornkamm, G. W. (1993). The Epstein-Barr virus nuclear antigen 2 interacts with an EBNA2 responsive cis-element of the terminal protein 1 gene promoter. *EMBO J.* 12, 167–175.

Zimber-Strobl, U., Strobl, L. J., Meitinger, C., Hinrichs, R., Sakai, T., Furukawa, T., Honjo, T. and Bornkamm, G. W. (1994). Epstein-Barr virus nuclear antigen 2 exerts its transactivating function through interaction with recombination signal binding protein RBP-Jκ, the homologue of drosophila suppressor of hairless. *EMBO J.* 13, 4973–4982.

What is claimed is:

1. A process for the preparation of human monoclonal anitibodies comprising the following steps of:

a) infecting or transfecting human antibody-producing B cells with an Epstein-Barr virus or a vector comprising Epstein-Barr virus nucleic acid sequences necessary for immortalization, in a first culture medium wherein said Epstein-Barr virus or vector expresses an Epstein-Barr virus nuclear antigen 2 (EBNA2) protein that is functional in said first culture medium, to produce immortalized B cells;

b) screening said immortalized B cells for specificity for a desired antigen to identify an immortalized B cell clone producing antibodies specific for the desired antigen;

c) propagating said identified B cell clone in said first culture medium;

d) culturing said propagated B cell clone in a second culture medium wherein the expression or function of said EBNA2 protein is reduced, and antibody production is thereby increased;

e) recovering antibodies from said second culture medium.

2. The process according to claim 1, wherein said Epstein-Barr virus or vector comprises a nucleotide sequence encoding EBNA2 fused, in functional connection, with a nucleotide sequence encoding a hormone-binding domain to produce a fusion gene encoding a fusion protein comprising EBNA2 and said hormone-binding domain.

3. The process according to claim 2, wherein said hormone-binding domain binds estrogen or an androgen.

4. The process according to claim 2, wherein said first culture medium comprises a hormone specific for said hormone-binding domain at a concentrarion sufficient to produce immortalized B cells, and said second culture medium comprises a sufficiently reduced concentration of said hormone, compared to said first culture medium, to increase antibody production by said propagated B cell clone.

5. The process according to claim 1, wherein said Epstein-Barr virus or vector comprises a nucleotide sequence encoding EBNA2 operatively linked with a nucleotide sequence that provides inducible expression of said nucleotide sequence encoding EBNA2.

6. The process according to claim 1, wherein said human antibody-producing B cells comprise primary human B cells derived from humans bearing antibodies directed against the desired antigen.

7. The process according to claim 1, wherein said EBNA2 protein is expressed as fusion protein with the hormone-binding domain of the estrogen receptor or said EBNA2 protein is expressed under the control of an inducible promoter.

8. The process according to claim 1, wherein said vector is an Epstein-Barr virus-derived vector.

9. The process according to claim 1, wherein said antibodies produced by said identified B cell clone are selected from the group consisting of IgM, IgG, and IgA.

10. The process according to claim 8, wherein said vector is a mini-EBV plasmid accompanied by a helper virus.

11. The process according to claim 7, wherein said expression of an EBNA2 protein is under the control of an inducible promoter, and wherein expression is induced by an inducer in step a), and said inducer is removed before step d).

* * * * *